(12) United States Patent
White et al.

(10) Patent No.: US 6,849,994 B1
(45) Date of Patent: Feb. 1, 2005

(54) ELECTRODE ASSEMBLY FOR LITHOTRIPTERS

(75) Inventors: Robert A. White, Cartersville, GA (US); Jeff T. McCain, Acworth, GA (US); David M. Loch, Dallas, GA (US)

(73) Assignee: HealthTronics Surgical Services, Inc., Marietta, GA (US)

( * ) Notice: Subject to any disclaimer, the term of this patent is extended or adjusted under 35 U.S.C. 154(b) by 51 days.

(21) Appl. No.: 10/610,401

(22) Filed: Jun. 30, 2003

(51) Int. Cl.[7] ............................................. H01T 13/24
(52) U.S. Cl. ....................................... 313/122; 313/125
(58) Field of Search ................................ 313/118, 122, 313/125, 135, 136, 141

(56) References Cited

U.S. PATENT DOCUMENTS 2,687,712 A * 8/1954 Wright ....................... 313/11.5

* cited by examiner

Primary Examiner—Vip Patel
(74) Attorney, Agent, or Firm—Stephen J. Stark; Miller & Martin PLLC

(57) ABSTRACT

An electrode assembly has an inner conductor removably connected to an insulating layer. The inner electrode is removable so that the discharge tip may be replaced without destroying the insulating layer and thus reused. In the preferred embodiment external threads on the inner conductor cooperate with internal threads in a bore of the insulating layer to fixably secure the insulating layer in a desired position relative to the inner conductor and discharge electrode tip. The discharge electrode is located colinearly with a grounded electrode tip spaced by a spark gap. The grounded electrode tip is also configured to be easily removed from the electrode assembly for replacement when degraded.

20 Claims, 4 Drawing Sheets

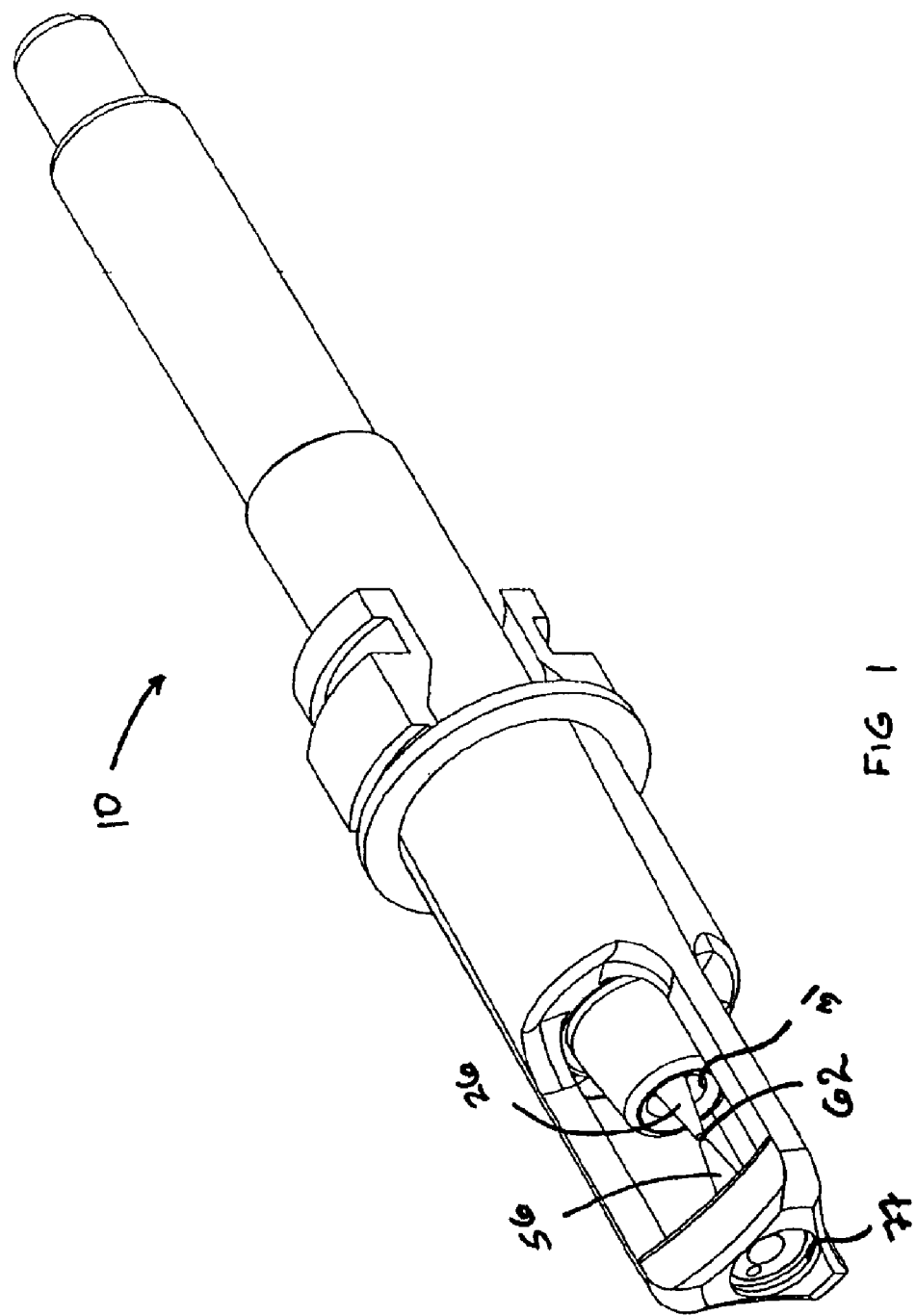

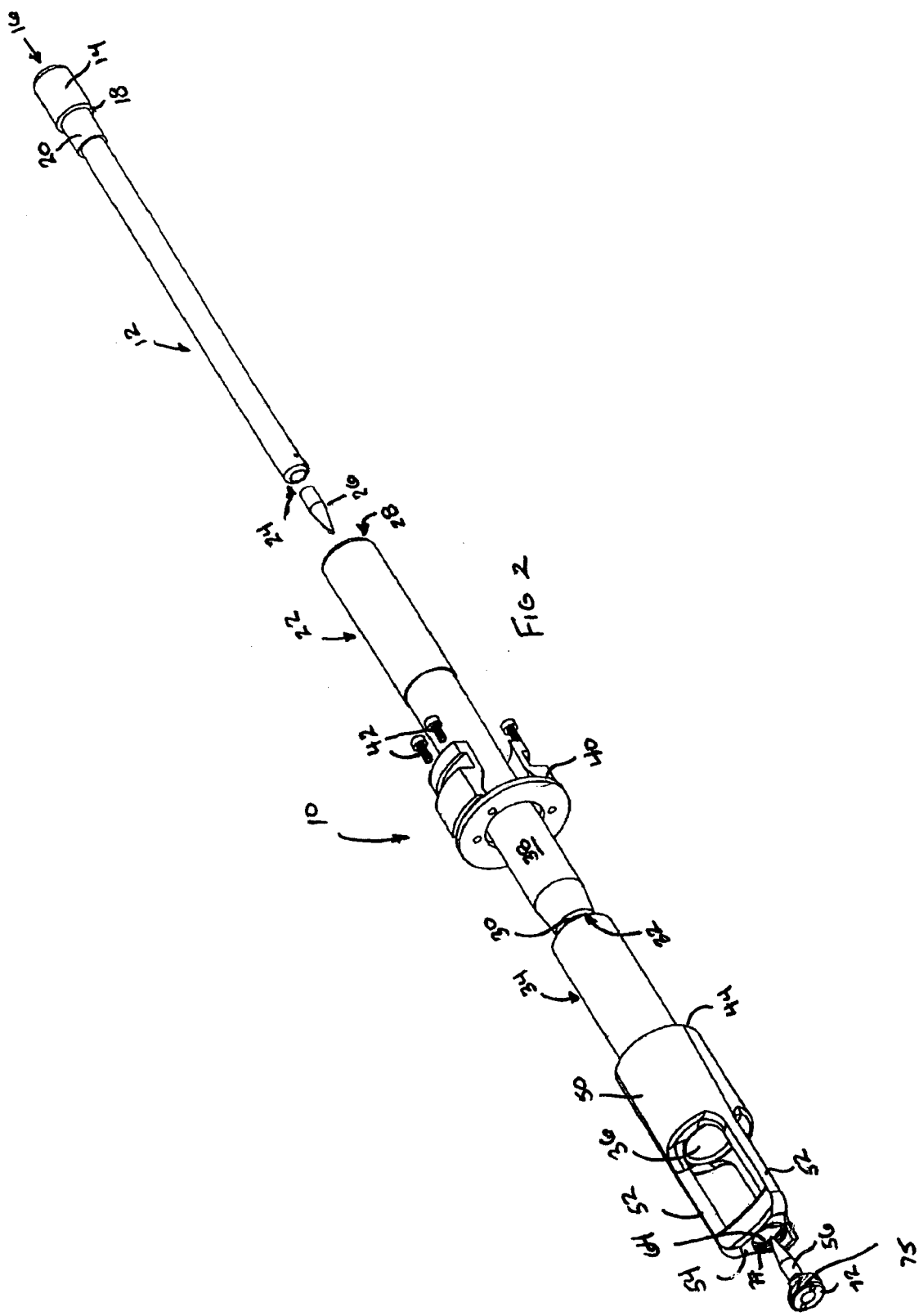

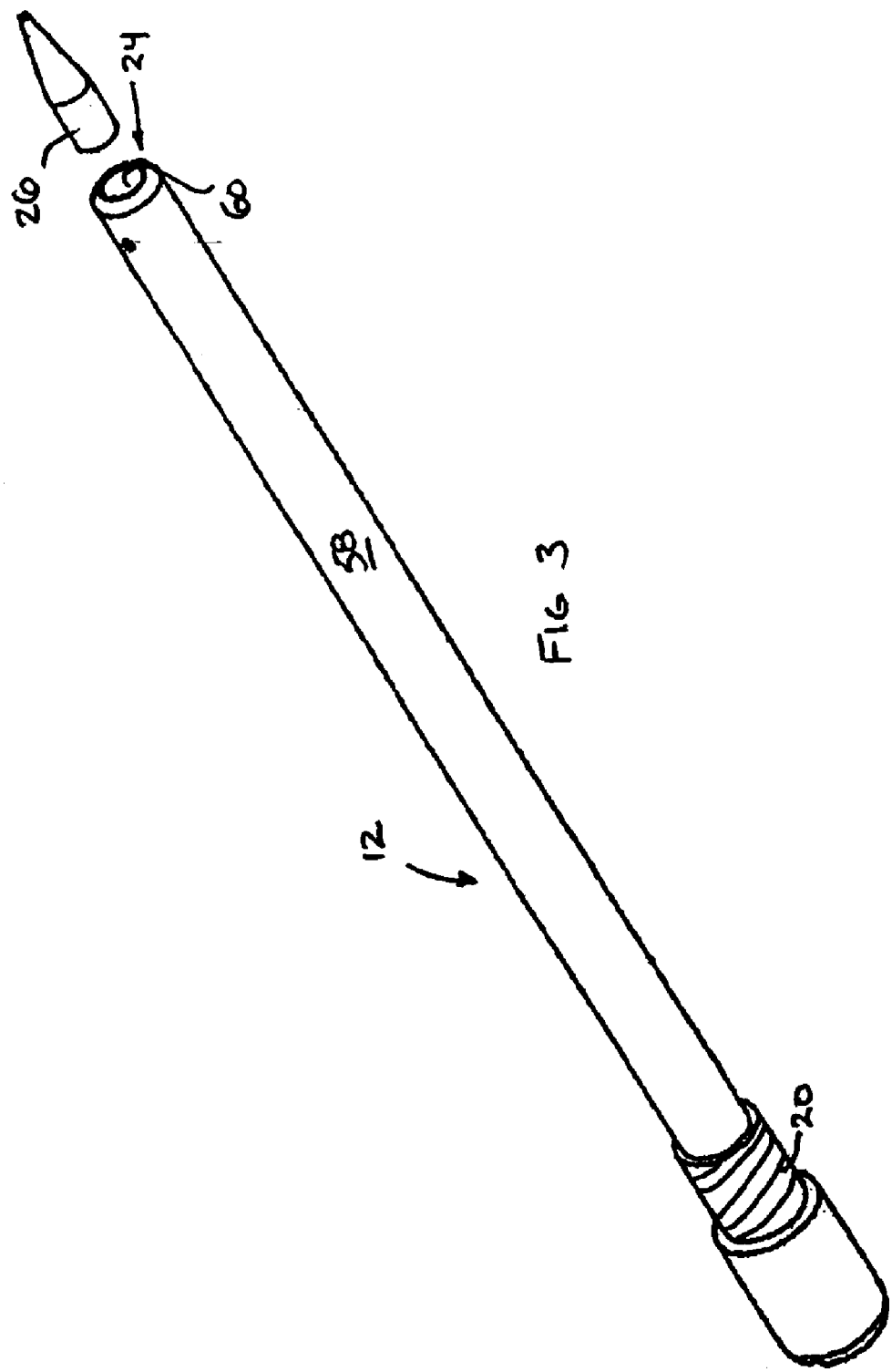

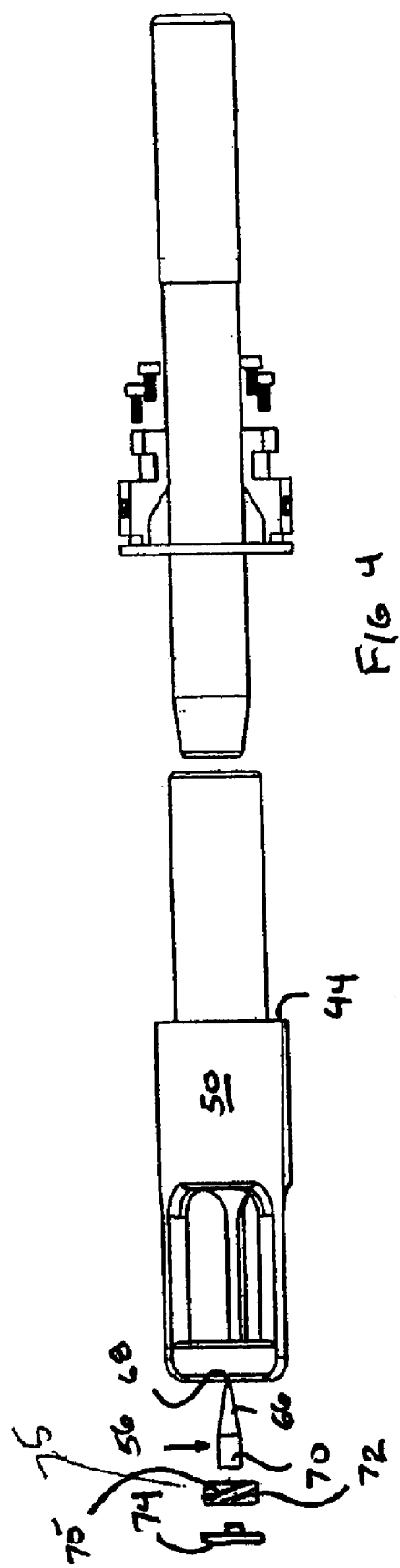

ELECTRODE ASSEMBLY FOR LITHOTRIPTERS

BACKGROUND OF THE INVENTION

1. Field of the Invention

The present invention relates generally to the field of lithotripters used for noninvasive fragmentation of concrements in living beings. More specifically, the present inventions disclose an improved electrode for lithotripters in which the discharge tips can be easily removed and replaced while maintaining the tolerance of the spark gap intermediate the discharge tips.

2. Description of Related Art

Conventional extra-corporeal lithotripters utilize shock waves to noninvasively fragment concrements within a patient. Most lithotripters are comprised of an electrode which generates a spark at a spark gap intermediate discharge tips. The spark is usually positioned within a reflector filled with a fluid. The presence of the spark in the fluid generates acoustic shock waves as a certain amount of water is flashed to steam. The shock wave passes through the reflector and through tissues of the patient until the concrement is contacted. A plurality of shock waves has been found effective at disintegrating many concrements.

The electrodes are usually constructed with an inner conductor which is surrounded by an insulative layer applied as a liquid and allowed to solidify about the inner conductor. The inner conductor terminates at a first electrode tip which extends from the insulative layer at a distal end of the inner conductor and insulative layer. An opposing second electrode tip is located collinearly with the first electrode tip to provide the spark gap there between. The first and second electrode tips are usually symmetrically located relative to one another about the spark gap. A cage provides a conductor and necessary structure to support the tip and to conduct electricity from an outer housing about the insulative layer to the second electrode tip. A clip is usually positioned about the housing to connect the electrode with a reflector and an electric supply.

Rapid and frequent discharges of energy across the electrode tips of the spark gap has been found to erode and/or deteriorate the electrode tips. Since the gap between the electrode tips is usually provided within relatively precise tolerances, most electrodes are not provided with an ability to replace either of the two opposing electrode tips. One attempt to provide an improved electrode can be seen in U.S. Pat. No. 5,420,473 which shows an insulative layer about the inner conductor equipped with threads which cooperate with inner threads on the housing so that the distance between opposing electrodes can be set to relatively precise tolerances simply by screwing the two together until a stop is contacted.

While the '473 patent reference shows a product that is an improvement over the prior art, this device still requires the replacement of the entire inner conductor/insulative layer assembly whenever the discharge electrode tip is degraded since the insulative layer must be machined off the inner doctor and a new one re-applied after replacing the electrode tip.

Accordingly an improved electrode is needed to overcome the limitations of the prior art.

SUMMARY OF THE INVENTION

It is an object of the invention to provide an improved electrode assembly for use with lithotripsy machines.

It is another object of the present invention to provide an electrode assembly having an inner conductor which is selectively removable from the insulating layer when the inner conductor may be removed, the discharge electrode tip replaced and then reconnected to the same insulative layer.

Accordingly, an electrode assembly of the preferred embodiment has an inner conductor extending from a proximal to a distal end whether received in or otherwise located at the distal end of the inner conductor. An insulating layer has a bore extending from the proximal end to a distal end of the insulating layer as received over the inner electrode and a portion of the discharge tip. Threads on an external portion of the inner electrode and internal threads on the bore of the insulating layer cooperate to selectively retain the insulating layer relative to the inner conductor until a stop is reached thereby securing the insulating layer relative to the inner conductor. A housing connected to a cage is positioned about the insulating layer and inner electrode to a grounded electrode tip which is located collinearly with the first electrode tip and separated by a spark gap there between.

BRIEF DESCRIPTION OF THE DRAWINGS

The particular features and advantages of the invention as well as other objects will become apparent from the following description taken in connection with the accompanying drawings in which:

FIG. 1 is a side perspective view of an assembled electrode assembly in accordance with the present preferred embodiment of the present invention;

FIG. 2 is an exploded view of component parts of the electrode assembly;

FIG. 3 is a detailed view of the inner conductor and first electrode tip; and

FIG. 4 is a detailed side exploded view of the cage assembly supporting the second electrode tip.

DETAILED DESCRIPTION OF THE DRAWINGS

FIG. 1 is a top perspective view of the preferred embodiment of an electrode assembly 10. Although the basic components of the assembled version of the electrode assembly 10 are not markedly different from those currently in use, the construction of this electrode assembly 10 is believed to have many advantages over the prior art.

FIG. 2 shows an exploded view of the electrode assembly 10 in component parts. The electrode assembly 10 is comprised of an inner conductor 12 which has a base 14 at its proximal end 16. In the preferred embodiment the base 14 terminates at ledge 18 where external threads 20 are located. The ledge 18 acts as a stop to prevent further insertion of the inner conductor 12 relative to the insulating layer 22. In the prior art, the insulating layer was applied as a liquid directly over the inner conductor 12 which was normally a brass cylindrical member which tapered towards its distal end 24. The insulated layer was normally a plastic that was molded about the inner conductor after installing first electrode tip or discharge tip 26 at the distal end 24 of the inner conductor 12. In fact, in the prior art, the insulating sleeve assisted in retaining the discharge electrode tip from being able to be removed from the inner conductor without first machining off such as by grinding the insulative layer. Accordingly, when the discharge tip became degraded, this would necessitate the machining off of the insulative layer, the replacement of the discharge tip and the reapplication of the insulating layer. This was a labor intensive practice.

In order to simplify the refurbishment process of discharge tips, the insulating layer 22 of the preferred embodiment is formed as a separate piece from the inner conductor 12. In fact it is constructed with an inner bore (obscured from view) which corresponds with a cooperating area with the reinserted portion of the inner conductor 12. At the proximal end 28 or other appropriate location within the bore of the insulating layer 22 are located inner threads which cooperate with the external threads 20 of the inner conductor 12 to secure the insulating layer 22 relative to the inner conductor 12. Of course, other stops and/or connectors could be utilized as well. At least a portion of the discharge tip 26 extends from opening 30 at the distal end 32 of the insulating layer 22 as shown in FIG. 1 when the insulating layer 22 is installed about the discharge tip 26 and inner conductor 12. The insulating layer 22 is thus relatively easily removed and reinstalled over the inner conductor 12.

The insulating layer 22 at the opening 30 has a concavity 31 as shown in FIG. 1 which extends about a portion of the first electrode tip 26. This concavity 31 or depression is useful in directing the spark intermediate the first electrode 26 and the second electrode tip 56, however, it need not be present in all embodiments.

The discharge tip, also known as lower tip or first electrode tip 26, can be formed so that the distance from the stop or ledge 18 to the distal end 24 of the inner conductor 12 and discharge tip 26 are within certain tolerances. After installing the insulating sleeve about the inner conductor 12 and first electrode tip 26, the housing 34 may be appropriately located relative to the insulating layer 22. The housing has an internal bore 36 which allows the housing 34 to be disposed about the exterior surface 38 of the insulating layer 22. The insulating layer 22 preferably contacts stop or ledge 18 when installed.

The housing 34 may be installed as is done in the prior art by heating the housing 34 and placing it about the insulating layer 22 to the desired position or otherwise. As the housing 34 cools, the bore 36 contracts about the exterior surface 38 of the insulating layer 22 to secure the housing 34 relative to the insulating layer 22. Of course, other methods of connecting the housing 34 to the insulating layer 22 may also be utilized as is known in the art.

The housing is preferably equipped with a plastic or other material clip 40 which is normally utilized on one side to connect to a electrical power connection and on the other side connect to a reflector. In the illustrated embodiment, the clip 40 is connected to the housing 34 as shown. Screws 42 are useful in securing the clip 40 to a ledge 44 on the housing 34. Of course, other connections may be utilized to connect the clip 40 relative to the housing 34. The housing 34 is illustrated integrally formed with cage base 50, but could also have external threads which cooperate with internal threads in a bore of cage base 50 or otherwise be connected to the cage base 50. Cage base 50 may be made to be easily removable from the housing 34 which acts as an outer conductor portion as does the cage base 50. The cage base 50 conducts electricity through arms 52 to upper tip holder 54 which receives the second electrode tip 56 as will be discussed in more detail below.

FIG. 3 shows a close-up view of the inner conductor 12 having the outer threads 20 which cooperate with inner threads on the insulating layer 22. Extending from the threads is cylindrical member 58 which terminates at the distal end 24 in a receiver 60 which receives the discharge electrode tip 26. Since the discharge tip 26 is preferably swedged or heat fit into the receiver 60 of the inner conductor 12, it can be relatively easily replaced by a manufacturer of electrode assemblies 10 without the need to perform machining operations to the inner conductor 12 apart from possibly heating the inner conductor 12 to cause the circumference of the receiver 60 to expand thereby allowing the discharge tip 26 to be removed. There is no need to grind off the insulating layer 22 since the insulating layer 22 may be unscrewed from the inner conductor 12 and reattached after replacement of the discharge electrode tip 26.

While other prior art electrode assemblies allow for replacement of the discharge tip 26 in a receiver 60, the insulating layer has to be machined away off of the inner conductor such as by grinding or otherwise. The ability to reuse insulating layers 22 is believed to be a huge improvement over the prior art as it drastically saves in man hours as well as in material cost.

FIG. 4 shows detail of the structure supporting the second electrode tip 56. The cage base 50 surrounds bore 36 which extends over the insulating layer 22 as well as the upper housing 44 shown in FIG. 2. The arms 52 are spaced apart providing access to the spark gap 62 shown in FIG. 1 which is the space directly between the electrode tips 26,56. Accordingly, when a spark is generated, the acoustic shock waves may be transmitted from the spark gap 62 through a reflector, if utilized, and on through the tissue of a patient to break up concrements.

While U.S. Pat. No. 5,420,473 shows a second electrode tip that is replaceable, it is not of the exact same configuration as the discharge electrode tip thereby requiring two separate parts to be manufactured. Accordingly, a need exists for the ability to interchange the first and second electrode tips 26,56 so that one part may be provided and utilized during the manufacturing processes. In the construction shown in the '473 patent, replacement of the second discharge tip with a first discharge tip will result in the second discharge tip falling out since there would be no way to easily retain it.

The cylindrical portion 70 of tip 56 is swedged or heat fitted into top 72. The top 72 is equipped with outer threads 75 which cooperate with internal threads 77 in the upper tip holder 54 which allow the top 72 to be replaced at a recycling facility. Cap 74 is preferably utilized to provide a smooth surface over the top 72. The point 68 extends through opening 64 to provide the spark gap 62 intermediate the tips 26,56 when installed.

Numerous alterations of the structure herein disclosed will suggest themselves to those skilled in the art. However, it is to be understood that the present disclosure relates to the preferred embodiment of the invention which is for purposes of illustration only and not to be construed as a limitation of the invention. All such modifications which do not depart from the spirit of the invention are intended to be included within the scope of the appended claims.

Having thus set forth the nature of the invention, what is claimed herein is:

1. An electrode assembly for use with lipotripters comprising:
   an inner electrode having a proximal and a distal end;
   a receiver located toward the distal end of the inner electrode;
   a first electrode tip in electrical communication with the receiver;
   an insulating layer having a proximal and a distal end defining a length therebetween and a bore extending the length of the insulating layer, said insulating layer detachably connected to the inner electrode with a portion of the first electrode tip extending beyond the distal end of the insulating layer when installed;

a stop limiting the travel of the bore of the insulating sleeve about the inner conductor in a direction from the distal end toward the proximal end of the inner conductor beyond a predetermined position;

an outer conductor located external to the insulating layer;

a second electrode tip spaced colinearly with the first electrode tip providing a spark gap therebetween, said second electrode tip in electrical communication with the outer conductor.

2. The electrode assembly of claim 1 wherein the outer conductor further comprises a cage extending from a housing wherein the housing is located coaxially with a longitudinal axis extending through the bore of the insulating layer.

3. The electrode assembly of claim 1 wherein the outer conductor is connected to the insulating layer.

4. The electrode assembly of claim 1 wherein the second electrode tip is retained by a removable tip holder in electrical communication with the outer conductor.

5. The electrode assembly of claim 4 wherein the second electrode tip is one of swedged and heat fit into a bore in the tip holder and the tip holder has external threads which cooperate with threads in a cap thereby retaining the second tip at a desired placement relative to the first tip.

6. The electrode assembly of claim 1 wherein the inner conductor further comprises threads which cooperate with threads in the bore of the insulating layer.

7. The electrode assembly of claim 1 wherein the first electrode tip is one of swedged and heat fit into the receiver.

8. The electrode assembly of claim 1 wherein the stop further comprises a shoulder on the inner conductor which contacts the insulative layer when fully installed relative to the inner conductor.

9. An electrode assembly for use in lithotripsy comprising:

an inner electrode having a proximal end and a distal end;

a receiver located toward the distal end of the inner electrode;

a first electrode tip contacting the receiver;

an insulating layer having a proximal and a distal end and a bore extending intermediate the proximate and the distal end along a longitudinal axis, said insulating layer detachably connected to the inner electrode with a portion of the first electrode tip extending beyond the distal end of the insulating layer when installed;

a stop limiting the travel of the bore of the insulating sleeve about the inner conductor in a direction from the distal end toward the proximal end of the inner conductor beyond a predetermined position;

an outer conductor secured to an external portion of the insulating layer; and a second electrode tip spaced oppositely and colinearly relative to the first electrode tip providing a spark gap between the first and second electrode tips, said second electrode tip in electrical communication with the outer conductor.

10. The electrode assembly of claim 9 wherein the first and second electrode tips each have a base at one end and a tapered section at an opposing end.

11. The electrode assembly of claim 10 wherein the tapered sections of the first and second electrode tips terminate respectively at rounded points and are interchangeable prior to being connected to one of the receiver and outer conductor.

12. The electrode assembly of claim 11 wherein the first electrode tip is secured to the receiver and the second electrode tip is retained by a top.

13. The electrode assembly of claim 12 wherein the top is threadably engaged in a tip holder, and the electrode tip is retained in a bore in the top.

14. The electrode assembly of claim 9 wherein the inner conductor has threads which cooperate with threads in the bore of the insulating layer when installed.

15. The electrode assembly of claim 14 wherein the threads on the inner conductor are located closer to the proximal end of the conductor than the distal end.

16. The electrode assembly of claim 15 wherein the stop is a shoulder formed intermediate the threads of the inner conductor and the proximal end of the conductor.

17. An electrode assembly for lithotripsy comprising:

an inner conductor having an exterior surface and a proximal and a distal end with a first electrode tip at the distal end of the inner conductor;

an insulating layer about a portion of the inner conductor, said insulating layer having a bore therethrough receiving the inner conductor therein;

a first connector portion formed into the exterior surface of the conductor which cooperates with second connector portion of the insulating layer to retain the insulating layer relative to the inner conductor;

a grounded second electrode tip colinearly spaced from the first electrode tip;

a housing having a passageway extending along a longitudinal axis through said housing intermediate a distal opening and a proximal opening;

a cage extending from a proximal end of the housing;

an end cap connected to the cage retaining the second electrode therein spaced by a spark gap from the first electrode tip.

18. The electrode assembly of claim 17 wherein the first and second connector portions are threads.

19. The electrode assembly of claim 17 further comprising a clip about the housing.

20. The electrode assembly of claim 17 wherein twisting of the inner conductor relative to the insulating layer in a first direction releases the first and second connector portions thereby allowing the inner conductor to be pulled out of the bore of the insulating layer.

* * * * *